United States Patent [19]

Espinel

[11] Patent Number: 5,464,018

[45] Date of Patent: Nov. 7, 1995

[54] EVALUATION OF SALT SENSITIVITY IN HYPERTENSION

[76] Inventor: Carlos H. Espinel, 3328 "O" St., N.W., Washington, D.C. 20007

[21] Appl. No.: 358,994

[22] Filed: Dec. 19, 1994

Related U.S. Application Data

[63] Continuation of Ser. No. 157,262, Nov. 26, 1993, abandoned.

[51] Int. Cl.$^6$ .................................................. A61B 5/021
[52] U.S. Cl. ............................................ 128/672; 128/898
[58] Field of Search ................................... 129/668, 670, 129/672–686, 898

[56] References Cited

FOREIGN PATENT DOCUMENTS

| 1225517 | 4/1986 | U.S.S.R. | 128/672 |
| 1387972 | 4/1988 | U.S.S.R. | 128/672 |
| 1398822 | 5/1988 | U.S.S.R. | 128/672 |

OTHER PUBLICATIONS

Espinel, "The Salt Step Test: Its Usage in the Diagnosis of Salt Sensitive Hypertension . . . ," *Journal of The Amer. College of Nutrition*, vol. 11, No. 5, 526–531 (1992).

Espinel, "The Salt Step Test . . . " ASH–May 1990—vol. 3, #5(2).

Federral Register, Janb, 1993 (report of Espinel).

*Primary Examiner*—Angela D. Sykes
*Attorney, Agent, or Firm*—Glenna Hendricks; Stephen Gates

[57] ABSTRACT

A method of evaluating salt sensitivity in a hypertensive patient comprises evaluating customary salt intake and deleting from the diet any substance other than salt that might influence blood pressure, feeding the patient a diet without restriction of salt and measuring blood pressure until blood pressure becomes stabilized at the hypertensive level or, if hypertension is not seen, for about 90 days, thereafter restricting the salt intake in the diet, and gradually increasing the salt intake and measuring blood pressure to determine when the blood pressure begins to rise during the period of increasing salt intake to determine salt sensitivity that gives rise to hypertension.

4 Claims, No Drawings

EVALUATION OF SALT SENSITIVITY IN HYPERTENSION

This application is a continuation of application Ser. No. 08/57,262, filed Nov. 26, 1993 now abandoned.

FIELD OF THE INVENTION

This invention relates to evaluation and treatment of hypertension, particularly as it relates to sodium intake of the patient.

BACKGROUND OF THE INVENTION

It is estimated that 40% of the United States adult population suffers from hypertension. (The American Heart Association guidelines indicate hypertension exists when the blood pressure is greater than 140/90 mm Hg.) Fifty percent of hypertension is believed linked to salt sensitivity. However, the degree to which sodium intake and hypertension are linked in cause-effect relationship has long been disputed. It is known that many hypertensive individuals respond to decrease in dietary sodium intake by decrease in blood pressure. It is also known that some hypertensive individuals fail to respond favorably to restricted salt diet. Some have recommended moderate dietary salt restriction for all patients. Restriction of salt is not without danger, particularly during hot weather or strenuous exercise. The failure of salt restrictions to control hypertension most likely arises from indiscriminate implementation of the restricted salt/sodium diet. Prediction of the effect of restriction of sodium intake in any particular patient may be an important factor in determining treatment protocol for the patient. Previously a patient was deemed salt-sensitive if $(SBP-DBP) \div 3 + (DBP)$ where SBP is systolic blood pressure and DBP is diastolic blood pressure showed >10 mm Hg increase in response to an administration of sodium chloride in amounts higher than the customary intake subsequent to administration of sodium chloride after depletion. (Causes of depletion may include administration of diuretic agents or severe dietary restrictions.) Methods of evaluation using these criteria were not found to be readily applicable. Failure to reflect customary habits and diet were probably factors that decreased applicability of the evaluative methods previously used.

SUMMARY OF THE INVENTION

It is the purpose of this invention to provide means for identifying patients that suffer from hypertension related to salt sensitivity. It is also a purpose of this invention to provide guidelines for choosing treatment modalities for patients suffering from hypertension. By methods of the invention it is possible to determine, not only the presence, but also the degree of salt sensitivity.

The method of the invention requires the steps of: (a) deleting from the diet any substance other than salt that might influence blood pressure; (b) while feeding the patient a diet without restriction of salt; (c) restricting diet to provide a no salt or low sodium diet; (d) gradually increasing amount of salt to determine at which level the blood pressure begins to increase. The blood pressure is checked frequently throughout the period to determine whether or not the amount of salt intake causes changes in the blood pressure. The salt used in the method of the invention is ordinary table salt.

DETAILED DESCRIPTION OF THE INVENTION

The invention is concerned with identifying persons with "salt-sensitive" hypertension. The test provides guidance in prescribing the appropriate salt content of the diet based on the individual patient needs as determined by the methods of the invention. The methods of the invention do not alter the patient's life-style unnecessarily nor require hospitalization or use of drugs. The salt-sensitive hypertensive patient is defined as one whose blood pressure lowers toward normal in response to a physiologic dietary salt restriction implemented with regular food, and whose blood pressure rises again with reentry of salt into the diet. The salt is added in measured increments until hypertensive levels of blood pressure are seen (called herein, the salt hypertension threshold). Treatment of the salt-sensitive patient requires instruction in dietary management.

In describing the test used (herein called the salt step test), hypertension is defined as a blood pressure (BP) of $\geq 140/90$. Isolated systolic hypertension (ISH) indicates a diastolic blood pressure (DBP) $\leq 90$ mm Hg and systolic blood pressure (SBP) of $\geq 140$ mm Hg. The test encompasses three phases (1) the unrestricted dietary salt phase, used to document hypertension and customary salt intake; (2) the restricted salt phase to identify the salt-sensitive patient; and (3) the stepwise-increased salt phase, which is used to find the level of salt that precipitates hypertension.

Throughout all phases of the testing, the patient ceases exposure to other medications or substances that are known to effect blood pressure or alter salt balance, such as antihypertensives, anti-inflammatory drugs, alcohol, etc. The blood pressure is checked frequently throughout all phases. To assure more uniform results, it is best to have the patient rest for at least 5 minutes in a sitting or supine position. The BP is then checked on the same arm three times, and the average of the last two measurements is used for the analysis. Korotkoff's criterion is used for BP measurements with a sphygmomanometer. A diastolic blood pressure value of $\geq 90$ or systolic blood pressure of $\geq 140$, either of which is confirmed on three readings is deemed hypertensive. The patient identified as hypertensive is placed on a non-salt diet for salt sensitivity identification, and is subsequently given stepwise increases in dietary salt until the salt hypertensive threshold is found. Once the salt sensitivity is identified and the threshold is found, the patient is placed on a diet restricted specifically below his or her threshold.

Blood pressure may also be measured by devices other than a sphygmomanometer. Mean arterial pressure calculated as $(SBP-DBP) \div 3 + (DBP)$ may be used to compare results with salt sensitive responses effected with previously described techniques.

Twenty-four-hour urine measurements of sodium, chloride and creatinine (used as an indicator of urine collection completeness) may be used to estimate salt intake. The average of two successive collections might be reported as a 24 hour urine study. Creatinine clearance and functional excretion of sodium are used when necessary to evaluate glomerular filtration rate and tubular reabsorption of sodium. When necessary, a patient's relatives may be recruited to assist with dietary management. Work, social and exercise routines are usually left unchanged.

Unrestricted Salt Phase:

After initial evaluation, the patient is instructed to discontinue pharmacological agents and other drugs such as alcohol which might effect test parameters. If the patient is taking agents that alter blood pressure or sodium balance, the 24-hour urine collection is begun immediately is the blood pressure and determined to evaluate whether or not hypertension exists. If the patient has been taking agents (including alcohol) which alter blood pressure or sodium balance, the test reading is required after eight to fifteen days. When the patient has been taking antihypertensive agents, the patient should be studied until blood pressure is stable at the hypertensive level or, if hypertension is not seen, for 90 days. In evaluating patients who have been exposed to agents effecting blood pressure or sodium balance, it is advisable to check the BP at least semiweekly for the first two weeks and, thereafter, at least weekly. Once the level of hypertension has been established, baseline evaluation, including 24 hour urine studies, are performed. Once the level of hypertension has been established, is baseline evaluation, including 24 hour urine studies, accomplished. Restricted Salt Phase:

The hypertensive patient is instructed in a dietary salt intake involving stepwise increases in salt. For example, sodium chloride levels may commence using 0.5, 1.0, or 2 g/day of salt in the diet. If the studies indicate extreme sensitivity to sodium, low sodium diets, such as 200 mg/day to 1200 mg/day are known and are prescribed. The diet can be a modification of one of the American Dietetic Association's sodium restriction diets or any other diet that provides normal daily nutritional requirements and allows for sodium chloride restrictions. The level of blood pressure considered for the definition of salt sensitivity is that which corresponds to the values at which hypertension occurs at the simultaneous 24 hour urine collections that reflect the patient's intake. That may be, for example, the hypertensive BP values at a urinary sodium chloride of 8, 17 or 34 mmol/24 hours corresponds to an 8, 17 or 34 mmol intake. If the DBP falls to <90 mm Hg during a period of restriction, the patient is considered to be salt sensitive hypertensive. If the mean arterial pressure falls ≦10 mm Hg, but the patient's SBP and DBP are not ≦140/90, the patient is considered "partial salt-sensitive. In patients with ISH (i.e., normal DBP and SBP ≧140), the patient is considered to be salt-sensitive if SBP falls ≧10 mm Hg, but is not ≦140 mm Hg. Once conditions of salt sensitivity are established, the patient is reevaluated using methods described herein, including simultaneous 24-hour urine studies.
Stepwise Increased Salt Phase:

The salt-sensitive hypertensive patient is instructed to increase dietary salt in ascending steps. Each step ("salt step") represents a particular amount of sodium chloride in the diet, such as 0.5 g/day, 1.0 g/day, 2.0 g/day. Each step lasts 3 to 15 days. For each salt step, the patient is given 0.5, 1.0, or 1.0 gram packets of sodium chloride and/or calibrated spoons or containers with which to measure the prescribed amount of salt that can be used. The salt step amount is mixed with the "non-salt' meals, with the requirement that the food containing the added salt be taken in full. Blood pressure is checked at each salt level. Stepwise progressive increase continues until DBP raises to ≧90 mm Hg. Stepwise progressive increase continues in the ISH patient until SBP rises to <140 mm Hg. At a DBP ≧90 mm Hg., and in ISH with SBP <140 mm Hg, the patient is reevaluated by means disclosed above, including the 24 hour urine studies (UNaCl). Thus, the patient's salt hypertension threshold is determined.
Abbreviated Salt Step Test:

The abbreviated salt step test requires (1) establishment of BP and customary salt intake;

(2) restricted salt phase at 2 grams/day sodium chloride for 2 weeks (a) If the BP is <140/90, do evaluative studies, including UNaCl.

(b) If the BP falls 10 mm Hg, but BP is not <140/90, consider patient partial salt-sensitive.

(c) If the BP <140/90, use evaluative studies using 24 hour UNaCl. Consider the patient salt sensitive hypertensive.

(3) Do stepwise increase salt phase* at salt hypertensive threshold, reevaluate.

*Stepwise increased salt phase =0.5 g NaCl/day, 1.0 g NaCl/day, 2.0 g NaCl/day, and 3/0 g NaCl/day, each step lasting 1–4 weeks. The patients often self-care, doing daily monitoring of BP, diet, body weight, and symptoms as instructed.

Salt Hypertension Threshold Diet:

Dietary salt is restricted to >1 g/day below the patients threshold. The salt hypertension threshold diet is <10 g/day of sodium chloride as follows:

For threshold ≧10: 8 g NaCl/day

For threshold 8–10: 6 g NaCl/day

For threshold 6–8: 4 g NaCl/day

For threshold 4–6: 2 g NaCl/day

For threshold 2–4: 1 g NaCl/day

For threshold <2: 0.5 g NaCl/day

The American Dietetic Association's regular diet, or to any other diet containing normal daily nutritional requirements, table salt and salt-containing food products are added or restricted to meet each subject's needs. As the patient establishes and follows the diet, observation is continued for BP, body weight and symptoms of hypertension. The goal is hypertension control with diet alone or minimal doses of adjuvant pharmacologic agents. If the BP <140/90, the patient is considered in control and encouraged to continue the diet and regular care. If BP is 140/90, 24 hour urine studies are done to assess compliance with diet. If compliance is confirmed, the patient is first retested using the salt step test to establish changes in the threshold, and—if the threshold has not change —the threshold diet is continued in conjunction with pharmacologic agents as need to achieve hypertension control.
Self-Care Salt Step Test:

This test can be performed by the patient at home under the direction of the physician. Instructions indicate that hypertension constitutes blood pressure of ≧140/90. The amount of salt may be precipitating hypertension. If the salt precipitates or worsens hypertension, the patient is considered either salt-sensitive or partially salt sensitive. The patient is instructed to check BP and body weight, and to collect 24-hour urine samples. The patient is instructed to stop all pharmaceutical agents, including non-prescription drugs and alcohol, for 1–2 weeks. The patient measures and records body weight and blood pressure every 1–3 days. He/she also makes a record of all food consumed and estimates the dietary salt intake using the food label as a source of information regarding sodium chloride content. The 24-hour UNaCl may also be evaluated. However, the UNaCl is not always essential.

The patient is then instructed to follow the restricted dietary salt routine, with appropriate measurement and recording of body weight and BP. Again, the 24-hour UNaCl test may be done to check accuracy of intake record. Instructions then indicate method of using the increased salt phase test with each step to be used 1 week. The patient is instructed to increase the salt only if the blood pressure is <140/90, and to continue to increase amount of NaCl until the BP is <140/90. Once the salt level gives a BP of >140/90 after a week of intake at the particular level, that level is recorded as the salt hypertension threshold. The patient is then instructed in the amount of salt appropriate for use in accord with the teachings above.

As indicated herein, it is possible to have the patient perform much of the testing used in the inventive methods. This greatly decreases cost of evaluation and treatment, and encourages the patient to take responsibility for his own health care.

The tests disclosed herein have been repeated on several patient and results have been shown to be reproducible and very predictive.

I claim:

1. A method of evaluating and treating hypertension due to salt sensitivity comprising the steps of:

(1) in a first phase, evaluating customary salt intake and deleting from the diet any substance other than salt that might influence blood pressure whilst feeding the patient a diet without restriction of salt and measuring blood pressure until blood pressure becomes stabilized at the hypertensive level or, if hypertension is not noted, for 90 days;

(2) after blood pressure has become stabilized at the hypertensive level, restricting the diet to provide a no-salt or low sodium diet; the (3) gradually increasing the amount of salt in the diet, beginning with 0.5 gr. salt and incrementally increasing salt intake with each increment being maintained for at least 3 days and measuring blood pressure to determine at what level of salt intake the blood pressure rises to determine the salt hypertension threshold; and (4) restricting salt in diet on the basis of salt hypertension threshold to more than 1 gram below the salt hypertension threshold.

2. A method of claim 1 wherein the patient is placed in a sitting or supine position at least 5 minutes before the blood pressure is measured.

3. A method of claim 2 wherein the blood pressure is checked at least three times.

4. A method of claim 1 wherein the intake of salt during the unrestricted salt phase is estimated by 24 hour urine.

* * * * *